(12) United States Patent
Bolin et al.

(10) Patent No.: US 7,947,728 B1
(45) Date of Patent: May 24, 2011

(54) INDOLE AND INDAZOLE ANALOGS AS GLYCOGEN SYNTHASE ACTIVATORS

(75) Inventors: David Robert Bolin, Montclair, NJ (US); Matthew Michael Hamilton, Hackettstown, NJ (US); Lee Apostle McDermott, Aspinwall, PA (US); Lin Yi, Basking Ridge, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/903,458

(22) Filed: Oct. 13, 2010

Related U.S. Application Data

(60) Provisional application No. 61/260,059, filed on Nov. 11, 2009.

(51) Int. Cl.
  *A01N 43/56* (2006.01)
  *A01N 43/38* (2006.01)
  *C07D 231/56* (2006.01)
  *C07D 209/04* (2006.01)

(52) U.S. Cl. ............... 514/406; 514/412; 548/361.1; 548/469

(58) Field of Classification Search ............ 514/406, 514/412; 548/261.1, 469
See application file for complete search history.

(56) References Cited

U.S. PATENT DOCUMENTS

| 2004/0266856 A1 | 12/2004 | Chu et al. |
| 2005/0095219 A1 | 5/2005 | Yang et al. |

FOREIGN PATENT DOCUMENTS

| DE | 2842243 | 10/1980 |
| DE | 4142514 | 6/1993 |
| WO | 9740017 | 10/1997 |
| WO | 2004058679 | 7/2004 |
| WO | 2005000781 | 1/2005 |
| WO | 2006058648 | 6/2006 |
| WO | 2007024922 | 3/2007 |
| WO | 2007044622 | 4/2007 |
| WO | 2008033455 | 3/2008 |

OTHER PUBLICATIONS

Terasaka et al., caplus an 2006:32063.*
International Search Report for Corresponding Appl. PCT/EP2010/066868 filed Jan. 14, 2011.

* cited by examiner

*Primary Examiner* — Sun Jae Y Loewe
(74) *Attorney, Agent, or Firm* — George W. Johnston; Dennis P. Tramaloni; Samuel H. Megerditchian

(57) ABSTRACT

Provided herein are compounds of the formula (I):

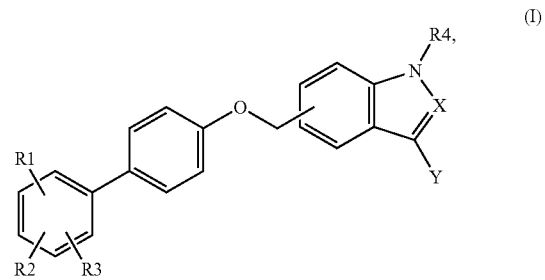

as well as pharmaceutically acceptable salts thereof, wherein the substituents are as those disclosed in the specification. These compounds, and the pharmaceutical compositions containing them, are useful for the treatment of metabolic diseases and disorders such as, for example, type II diabetes mellitus.

16 Claims, No Drawings

INDOLE AND INDAZOLE ANALOGS AS GLYCOGEN SYNTHASE ACTIVATORS

PRIORITY TO RELATED APPLICATION(S)

This application claims the benefit of U.S. Provisional Application No. 61/260,059, filed Nov. 11, 2009, which is hereby incorporated by reference in its entirety.

FIELD OF THE INVENTION

The invention is directed to compounds, salts and pharmaceutical compositions useful as activators of glycogen synthase for the treatment of metabolic diseases and disorders.

All documents cited or relied upon below are expressly incorporated herein by reference.

BACKGROUND OF THE INVENTION

Diabetes mellitus is a common and serious disorder, affecting 10 million people in the U.S. [Harris, M. I. Diabetes Care 1998 21 (3S) Supplement, 11C], putting them at increased risk of stroke, heart disease, kidney damage, blindness, and amputation. Diabetes is characterized by decreased insulin secretion and/or an impaired ability of peripheral tissues to respond to insulin, resulting in increased plasma glucose levels. The incidence of diabetes is increasing, and the increase has been associated with increasing obesity and a sedentary life. There are two forms of diabetes: insulin-dependent and non-insulin-dependent, with the great majority of diabetics suffering from the non-insulin-dependent form of the disease, known as type 2 diabetes or non-insulin-dependent diabetes mellitus (NIDDM). Because of the serious consequences, there is an urgent need to control diabetes.

Treatment of NIDDM generally starts with weight loss, a healthy diet and an exercise program. However, these factors are often unable to control the disease, and there are a number of drug treatments available, including insulin, metformin, sulfonylureas, acarbose, and thiazolidinediones. Each of these treatments has disadvantages and there is an ongoing need for new drugs to treat diabetes.

Metformin is an effective agent that reduces fasting plasma glucose levels and enhances the insulin sensitivity of peripheral tissue, mainly through an increase in glycogen synthesis [De Fronzo, R. A. Drugs 1999, 58 Suppl. 1, 29]. Metformin also leads to reductions in the levels of LDL cholesterol and triglycerides [Inzucchi, S. E. JAMA 2002, 287, 360]. However, it loses its effectiveness over a period of years [Turner, R. C. et al. JAMA 1999, 281, 2005].

Thiazolidinediones are activators of the nuclear receptor peroxisome-proliferator activated receptor-gamma. They are effective in reducing blood glucose levels, and their efficacy has been attributed primarily to decreasing insulin resistance in skeletal muscle [Tadayyon, M. and Smith, S. A. Expert Opin. Investig. Drugs 2003, 12, 307]. One disadvantage associated with the use of thiazolidinediones is weight gain.

Sulfonylureas bind to the sulfonylurea receptor on pancreatic beta cells, stimulate insulin secretion, and consequently reduce blood glucose levels. Weight gain is also associated with the use of sulfonylureas [Inzucchi, S. E. JAMA 2002, 287, 360] and, like metformin, they lose efficacy over time [Turner, R. C. et al. JAMA 1999, 281, 2005]. A further problem often encountered in patients treated with sulfonylureas is hypoglycemia [Salas, M. and Caro, J. J. Adv. Drug React. Tox. Rev. 2002, 21, 205-217].

Acarbose is an inhibitor of the enzyme alpha-glucosidase, which breaks down disaccharides and complex carbohydrates in the intestine. It has lower efficacy than metformin or the sulfonylureas, and it causes intestinal discomfort and diarrhea which often lead to the discontinuation of its use [Inzucchi, S. E. JAMA 2002, 287, 360].

Because none of these treatments is effective over the long term without serious side effects, there is a need for new drugs for the treatment of type 2 diabetes.

In skeletal muscle and liver, there are two major pathways of glucose utilization: glycolysis, or oxidative metabolism, where glucose is oxidized to pyruvate; and glycogenesis, or glucose storage, where glucose is stored in the polymeric form glycogen. The key step in the synthesis of glycogen is the addition of the glucose derivative UDP-glucose to the growing glycogen chain, and this step is catalyzed by the enzyme glycogen synthase [Cid, E. et al. J. Biol. Chem. 2000, 275, 33614]. There are two isoforms of glycogen synthase, found in liver [Bai, G. et al. J. Biol. Chem. 1990, 265, 7843] and in other peripheral tissues including muscle [Browner, M. F. et al. Proc. Nat. Acad. Sci. U.S.A. 1989, 86, 1443]. There is clinical and genetic evidence implicating both forms of glycogen synthase in metabolic diseases such as type 2 diabetes and cardiovascular disease. Both basal and insulin-stimulated glycogen synthase activity in muscle cells from diabetic subjects were significantly lower than in cells from lean non-diabetic subjects [Henry, R. R. et al. J. Clin. Invest. 1996, 98, 1231-1236; Nikoulina, S. E. et al. J. Clin. Enocrinol. Metab. 2001, 86, 4307-4314]. Furthermore, several studies have shown that levels of muscle [Eriksson, J. et al. N. Engl. J. Mod. 1989, 331, 337; Schulman, R. G. et al. N. Engl. J. Med. 1990, 332, 223; Thorburn, A. W. et al. J. Clin. Invest. 1991, 87, 489] and liver [Krssak, M. et. al. Diabetes 2004, 53, 3048] glycogen are lower in diabetic patients than in control subjects. In addition, genetic studies have shown associations in several populations between type 2 diabetes and/or cardiovascular disease and mutation/deletion in the GYS1 gene encoding the muscle isoform of glycogen synthase [Orhu-Melander, M. et al. Diabetes 1999, 48, 918; Fredriksson, J. et. al. PLoS ONE 2007, 3, e285; Kolhberg G. et. al. N. Engl. J. Med. 2007, 357, 1507]. Patients lacking GYS2 encoding the liver isoform of glycogen synthase, suffer from fasting ketotic hypoglycemia and postprandial hyperglycemia, hyperlactanemia and hyperlipidemia, supporting the essential role of liver GS in maintaining normal nutrient metabolism. [Weinstein, D. A. et. al. Mol. Genetics and Metabolism, 2006, 87, 284]

Glycogen synthase is subject to complex regulation, involving phosphorylation in at least nine sites [Lawrence, J. C., Jr. and Roach, P. J. Diabetes 1997, 46, 541]. The dephosphorylated form of the enzyme is active. Glycogen synthase is phosphorylated by a number of enzymes of which glycogen synthase kinase 3β (GSK3β) is the best understood [Tadayyon, M. and Smith, S. A. Expert Opin. Investig. Drugs 2003, 12, 307], and glycogen synthase is dephosphorylated by protein phosphatase type I (PP1) and protein phosphatase type 2A (PP2A). In addition, glycogen synthase is regulated by an endogenous ligand, glucose-6-phosphate which allosterically stimulates the activity of glycogen synthase by causing a change in the conformation of the enzyme that renders it more susceptible to dephosphorylation by the protein phosphatases to the active form of the enzyme [Gomis, R. R. et al. J. Biol. Chem. 2002, 277, 23246].

Several mechanisms have been proposed for the effect of insulin in reducing blood glucose levels, each resulting in an increase in the storage of glucose as glycogen. First, glucose uptake is increased through recruitment of the glucose transporter GLUT4 to the plasma membrane [Holman, G. D. and Kasuga, M. Diabetologia 1997, 40, 991]. Second, there is an increase in the concentration of glucose-6-phosphate, the allosteric activator of glycogen synthase [Villar-Palasi, C. and Guinovart, J. J. FASEB J. 1997, 11, 544]. Third, a kinase cascade beginning with the tyrosine kinase activity of the insulin receptor results in the phosphorylation and inactivation of GSK3β, thereby preventing the deactivation of glycogen synthase [Cohen, P. Biochem. Soc. Trans. 1993, 21, 555; Yeaman, S. J. Biochem. Soc. Trans. 2001, 29, 537].

Because a significant decrease in the activity of glycogen synthase has been found in diabetic patients, and because of its key role in glucose utilization, the activation of the enzyme glycogen synthase holds therapeutic promise for the treatment of metabolic diseases such as type 2 diabetes and cardiovascular diseases. The only known allosteric activators of the enzyme are glucose-6-phosphate [Leloir, L. F. et al. Arch. Biochem. Biophys. 1959, 81, 508] and glucosamine-6-phosphate [Virkamaki, A. and Yki-Jarvinen, H. Diabetes 1999, 48, 1101].

The following biaryloxymethylarenecarboxylic acids are reported to be commercially available from Otava, Toronto, Canada, Akos Consulting & Solutions, Steinen, Germany or Princeton BioMolecular Research, Monmouth Junction, N.J.: 4-(biphenyl-4-yloxymethyl)-benzoic acid, 3-(biphenyl-4-yloxymethyl)-benzoic acid, [4-(biphenyl-4-yloxymethyl)-phenyl]-acetic acid, [4-(4'-methyl-biphenyl-4-yloxymethyl)-phenyl]-acetic acid, 4-(4'-methyl-biphenyl-4-yloxymethyl)-benzoic acid, 3-(3-bromo-biphenyl-4-yloxymethyl)-benzoic acid, [4-(3-bromo-biphenyl-4-yloxymethyl)-phenyl]-acetic acid, 2-(4'-methyl-biphenyl-4-yloxymethyl)-benzoic acid, 5-(biphenyl-4-yloxymethyl)-furan-2-carboxylic acid, 5-(4'-methyl-biphenyl-4-yloxymethyl)-furan-2-carboxylic acid, 5-(3-bromo-biphenyl-4-yloxymethyl)-furan-2-carboxylic acid, 4-(biphenyl-4-yloxymethyl)-5-methyl-furan-2-carboxylic acid, 5-methyl-4-(4'-methyl-biphenyl-4-yloxymethyl)-furan-2-carboxylic acid, 4-(3-bromo-biphenyl-4-yloxymethyl)-5-methyl-furan-2-carboxylic acid, 2-(biphenyl-4-yloxymethyl)-4-methyl-thiazole-5-carboxylic acid, [2-(biphenyl-4-yloxymethyl)-thiazol-4-yl]-acetic acid, [2-(4'-methyl-biphenyl-4-yloxymethyl)-thiazol-4-yl]-acetic acid and [5-(biphenyl-4-yloxymethyl)-[1,3,4]oxadiazol-2-yl]-acetic acid.

Some biaryloxymethylarenecarboxylic acids are known in the art. However, none of these known compounds have been associated with either the treatment of diseases mediated by the activation of the glycogen synthase enzyme or to any pharmaceutical composition for the treatment of diseases mediated by the activation of the glycogen synthase enzyme. Andersen, H. S. et al. WO 9740017 discloses the structure and synthetic route to 3-(biphenyl-4-yloxymethyl)-benzoic acid as an intermediate in the synthesis of SH2 inhibitors. Winkelmann, E. et al. DE 2842243 discloses 5-(biphenyl-4-yloxymethyl)-thiophene-2-carboxylic acid as a hypolipemic agent. Mueller, T. et al. DE 4142514 discloses 2-(biphenyl-3-yloxymethyl)-benzoic acid as a fungicide. Ghosh, S. S. et al. WO 2004058679 discloses biaryloxymethylarene acids as ligands of adenine nucleoside translocase. Van Zandt, M. C. WO 2008033455 discloses biphenyl and heteroarylphenyl derivatives as protein phosphatase-1B inhibitors.

Glycogen synthase activators and stimulators of glycogen production have been reported. Chu, C. A et al. US 20040266856 discloses biaryoxymethylarenecarboxylic acids as glycogen synthase activators. Chu, C. A. WO 2005000781 discloses biaryloxymethylarene carboxylic acids as activators of glycogen synthase. Yang, S-P. and Huang, Y. US 20050095219 discloses hyaluronic acid compounds that stimulate glycogen production. Gillespie, P. et al. WO 2005075468 discloses biaryoxymethylarene carboxylic acids as glycogen synthase activators. Gillespie, P. et al. WO 2006058648 discloses biaryoxymethylarene carboxylic acids as glycogen synthase activators. Bucala, R. et al. WO 2007044622 discloses macrophage migration inhibitory factor agonists that stimulate glycogen production.

SUMMARY OF THE INVENTION

The present invention is directed to compounds of the formula I:

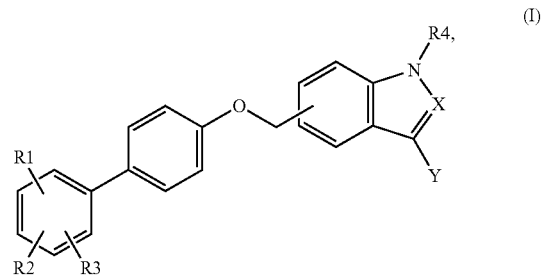

as well as pharmaceutically acceptable salts thereof, pharmaceutical compositions containing them and to methods of treating diseases and disorders. The compounds and compositions disclosed herein are glycogen synthase activators and are useful for the treatment of metabolic diseases and disorders, preferably diabetes mellitus, more preferably type II diabetes mellitus.

DETAILED DESCRIPTION OF THE INVENTION

In an embodiment of the present invention, provided is a compound of formula (I):

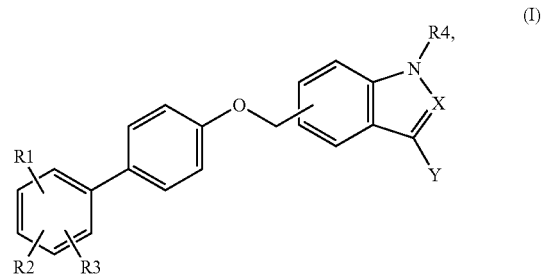

wherein,
R1, R2, R3, independently of each other, is hydrogen, halogen, lower alkyl or alkoxy;
R4 is hydrogen, unsubstituted lower alkyl, or lower alkyl substituted with one to four substituents independently selected from the group consisting of methyl, (=O) and —COOH;
X is CH or N; and
Y is hydrogen or —NH$_2$,
or a pharmaceutically acceptable salt thereof.
Preferably, R1, R2, R3, independently of each other, is halogen, lower alkyl or alkoxy.
Preferably, R1, R2, R3, independently of each other, is fluorine, chlorine, methyl or methoxy.
Preferably, R1 and R2 are halogen.
Preferably, R1 is fluorine or chlorine. Preferably, R2 is fluorine or chlorine.

Preferably, R3 is halogen or alkoxy. Preferably, R3 is fluorine or methoxy.

Preferably, R4 is lower alkyl substituted with one to four substituents independently selected from the group consisting of methyl, (=O) and —COOH.

Preferably, R4 is:

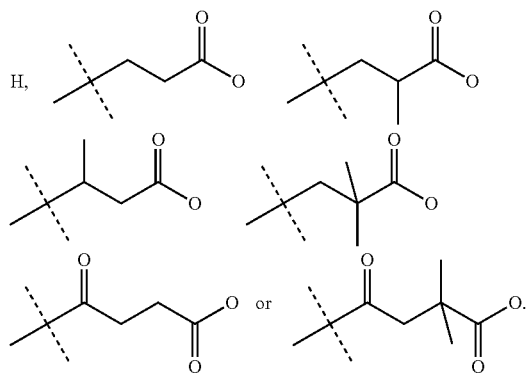

Preferably, X is CH.
Preferably, X is N.
Preferably, Y is hydrogen.
Preferably, Y is —NH$_2$.
Preferably, the compound according to formula (I) is:
4-(4',5'-Difluoro-2'-methoxy-biphenyl-4-yloxymethyl)-1H-indazole;
3-[4-(4',5'-Difluoro-2'-methoxy-biphenyl-4-yloxymethyl)-indazol-1-yl]-propionic acid;
6-(4',5'-Difluoro-2'-methoxy-biphenyl-4-yloxymethyl)-1H-indazole;
[6-(4',5'-Difluoro-2'-methoxy-biphenyl-4-yloxymethyl)-indazol-1-yl]-acetic acid;
3-[6-(4',5'-Difluoro-2'-methoxy-biphenyl-4-yloxymethyl)-indazol-1-yl]-propionic acid;
6-(4',5'-difluoro-2'-methoxy-biphenyl-4-yloxymethyl)-1H-indole;
3-[6-(4',5'-Difluoro-2'-methoxy-biphenyl-4-yloxymethyl)-indol-1-yl]-propionic acid;
[6-(4',5'-Difluoro-2'-methoxy-biphenyl-4-yloxymethyl)-indol-1-yl]-acetic acid;
3-[6-(4',5'-Difluoro-2'-methoxy-biphenyl-4-yloxymethyl)-indol-1-yl]-butyric acid;
4-(4',5'-Difluoro-2'-methoxy-biphenyl-4-yloxymethyl)-1H-indole;
4-[4-(4',5'-Difluoro-2'-methoxy-biphenyl-4-yloxymethyl)-indol-1-yl]-4-oxo-butyric acid;
4-[4-(4',5'-Difluoro-2'-methoxy-biphenyl-4-yloxymethyl)-indol-1-yl]-2,2-dimethyl-4-oxo-butyric acid;
[4-(4',5'-Difluoro-2'-methoxy-biphenyl-4-yloxymethyl)-indol-1-yl]-acetic acid;
3-[4-(4',5'-Difluoro-2'-methoxy-biphenyl-4-yloxymethyl)-indol-1-yl]-propionic acid;
3-[4-(4',5'-Difluoro-2'-methoxy-biphenyl-4-yloxymethyl)-indol-1-yl]-butyric acid;
5-(4',5'-Difluoro-2'-methoxy-biphenyl-4-yloxymethyl)-1H-indazol-3-ylamine; or
Methyl-5-(2',4',5'-trifluoro-biphenyl-4-yloxymethyl)-1H-indazol-3-ylamine.

In another embodiment, provided is a pharmaceutical composition, comprising a therapeutically effective amount of a compound according to formula (I), or a pharmaceutically acceptable salt thereof, and a pharmaceutically acceptable carrier and/or adjuvant.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, bornyl, adamantyl, indenyl and the like. In a preferred embodiment, the "cycloalkyl" moieties can optionally be substituted with one, two, three or four substituents with the understanding that said substituents are not, in turn, substituted further unless indicated otherwise in the Examples or claims below. Each substituent can independently be, for example, alkyl, alkoxy, halogen, amino, hydroxyl or oxygen (O=) unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate, with the understanding that said substituents are not, in turn, substituted further unless indicated otherwise in the Examples or claims below.

The term "lower alkyl", alone or in combination with other groups, refers to a branched or straight-chain alkyl radical of one to nine carbon atoms, preferably one to six carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, napthyl, 1,2,3,4-tetrahydronaphthalene, 1,2-dihydronaphthalene, indanyl, 1H-indenyl and the like.

The alkyl, lower alkyl and aryl groups may be substituted or unsubstituted. When substituted, there will generally be, for example, 1 to 4 substituents present, with the understanding that said substituents are not, in turn, substituted further unless indicated otherwise in the Examples or claims below. Substituents may include, for example, halogen, methyl, (=O), alkoxy and carboxylic acid.

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. The heteroaryl group may be substituted independently with one, two, or three substituents, with the understanding that said substituents are not, in turn, substituted further unless indicated otherwise in the Examples or claims below. Substituents may include, for example, lower alkyl and halogen.

As used herein, the term "alkoxy" means alkyl-O—; and "alkoyl" means alkyl-CO—. Alkoxy substituent groups or alkoxy-containing substituent groups may be substituted by, for example, one or more alkyl groups with the understanding that said substituents are not, in turn, substituted further unless indicated otherwise in the Examples or claims below.

As used herein, the term "halogen" means a fluorine, chlorine, bromine or iodine radical, preferably a fluorine, chlorine or bromine radical, and more preferably a fluorine or chlorine radical.

Compounds of formula (I) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

It will be appreciated, that the compounds of general formula (I) in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Compounds of the present invention can be prepared beginning with commercially available starting materials and utilizing general synthetic techniques and procedures known to those skilled in the art. Outlined below are reaction schemes suitable for preparing such compounds. Further exemplification can be found in the specific Examples detailed below.

Chemicals may be purchased from companies such as for example Aldrich, Argonaut Technologies, VWR and Lancaster. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Multigram II Mettler Toledo Instrument Newark, Del. Biotage, ISCO and Analogix columns are pre-packed silica gel columns used in standard chromatography.

Definitions as used herein include:
GS is glycogen synthase,
THF is tetrahydrofuran,
DMF is N,N-dimethylformamide,
DMA is N,N-dimethylacetamide,
DMSO is dimethylsulfoxide,
DCM is dichloromethane, DME is dimethoxyethane,
MeOH is methanol,
EtOH is ethanol,
NaOH is sodium hydroxide,
TFA is 1,1,1-trifluoroacetic acid,
HOBT is 1-hydroxybenzotriazole,
PyBroP is bromotripyrrolidinophosphonium hexafluorophosphate,
EDCI is 1-[3-(dimethylamino)propyl]-3-ethylcarbodiimide hydrochloride,
DIPEA is diisopropylethylamine,
Boc is tert-butyloxycarbonyl,
NBS is N-bromosuccinimde,
Brine is saturated aqueous sodium chloride solution,
TLC is thin layer chromatography,
RP HPLC is reversed phase high performance liquid chromatography,
HR-MS is high resolution mass spectrometry,
LC-MS is liquid chromatographic mass spectrometry,
RT is room or ambient temperature.

The preparation of substituted biphenylphenols is described in Scheme 1, below. Commercially available phenylboronic acid (i) can be coupled with 4-iodophenol under palladium catalysis conditions to form the bi-aryl-phenol (ii), where R1, R2 and R3 can be fluoro, chloro, methyl or methoxy groups. Alternatively, the required biphenylphenol (iv) can also be prepared through the coupling of 4-hydroxy-arylboronic acid with the corresponding arylbromide under palladium catalysis conditions (Scheme 1). Non-commercially available arylbromides (v) can be prepared through aromatic bromination.

with acetic anhydride and iso-amyl-nitrite in the presence of potassium carbonate and a phase transfer catalyst such as 18-crown-6 to give the bis-acetyl indazole vii. Upon treatment with HBr followed by tetrahydropyran, the bromomethyl derivative viii may be obtained. Compound viii can be alkylated with a substituted bi-aryl-phenol under basic conditions to form a substituted-bi-phenyloxymethyl-indazole (ix), which may be deprotected under acidic conditions, such as HCl or TFA in various solvents to give substituted-bi-phenyloxymethyl-indazole (x), where R1, R2 and R3 may be fluoro, chloro, methyl or methoxy. Xi may be treated with a bromoacetate or bromopropionate under basic conditions, such as lithium bis(trimethylsilyl)amide or cesium carbonate to give ester xi, which may be hydrolyzed to acid xii, where R1, R2 and R3 may be fluoro, chloro, methyl or methoxy and R4 may be a lower alkyl.

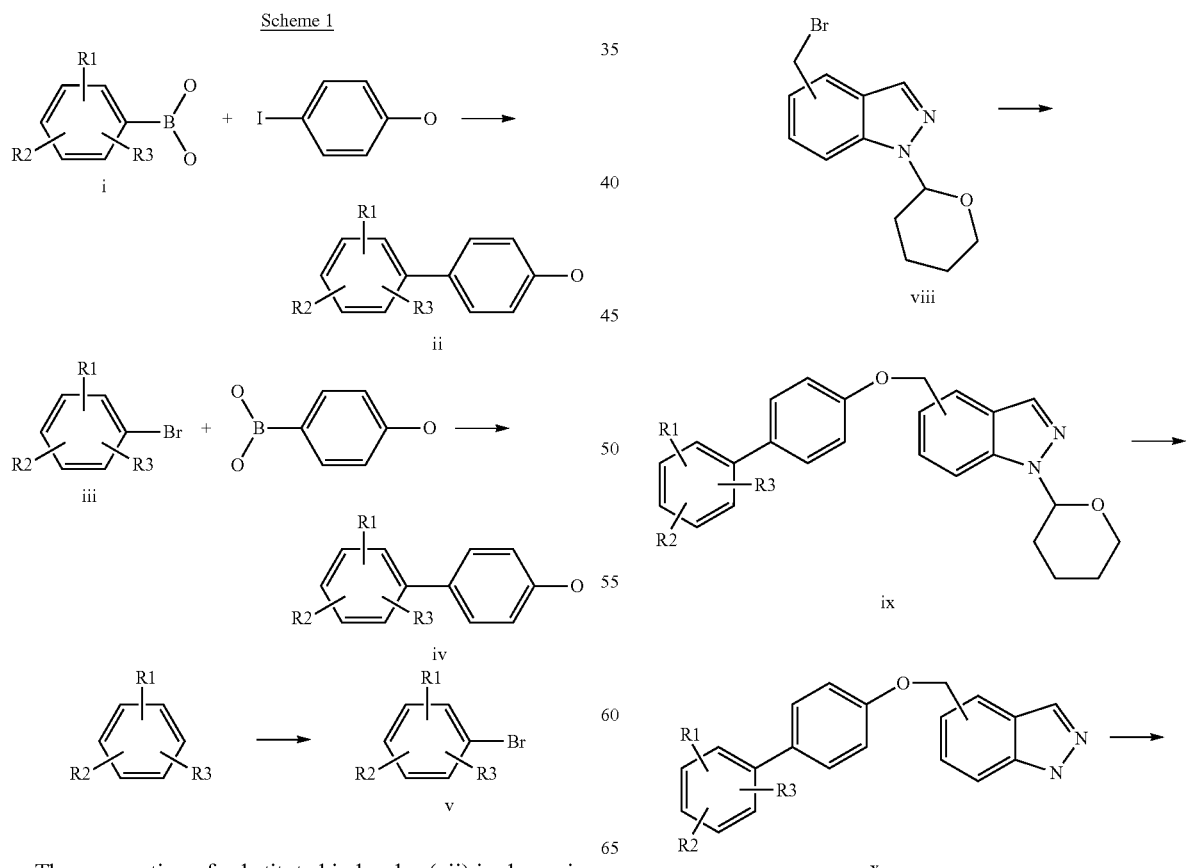

The preparation of substituted indazoles (xii) is shown in Scheme 2. Amino-methyl benzyl alcohol (vi) can be treated

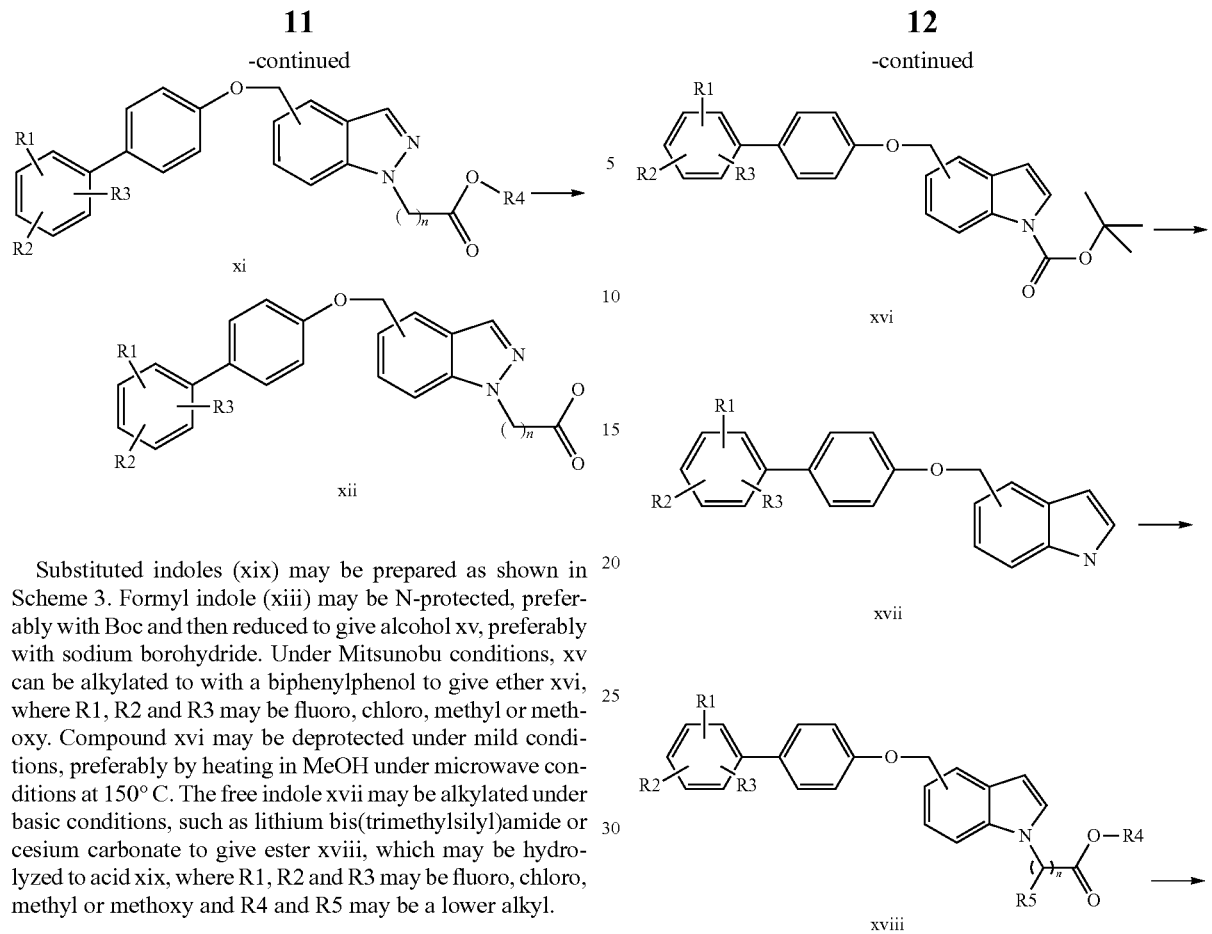

Substituted indoles (xix) may be prepared as shown in Scheme 3. Formyl indole (xiii) may be N-protected, preferably with Boc and then reduced to give alcohol xv, preferably with sodium borohydride. Under Mitsunobu conditions, xv can be alkylated to with a biphenylphenol to give ether xvi, where R1, R2 and R3 may be fluoro, chloro, methyl or methoxy. Compound xvi may be deprotected under mild conditions, preferably by heating in MeOH under microwave conditions at 150° C. The free indole xvii may be alkylated under basic conditions, such as lithium bis(trimethylsilyl)amide or cesium carbonate to give ester xviii, which may be hydrolyzed to acid xix, where R1, R2 and R3 may be fluoro, chloro, methyl or methoxy and R4 and R5 may be a lower alkyl.

As shown in Scheme 4, the free indole xvii may be acylated under basic conditions, such as lithium bis(trimethylsilyl)amide or cesium carbonate to give acid xx, where R1, R2 and R3 may be fluoro, chloro, methyl or methoxy and R6 may be a lower alkyl.

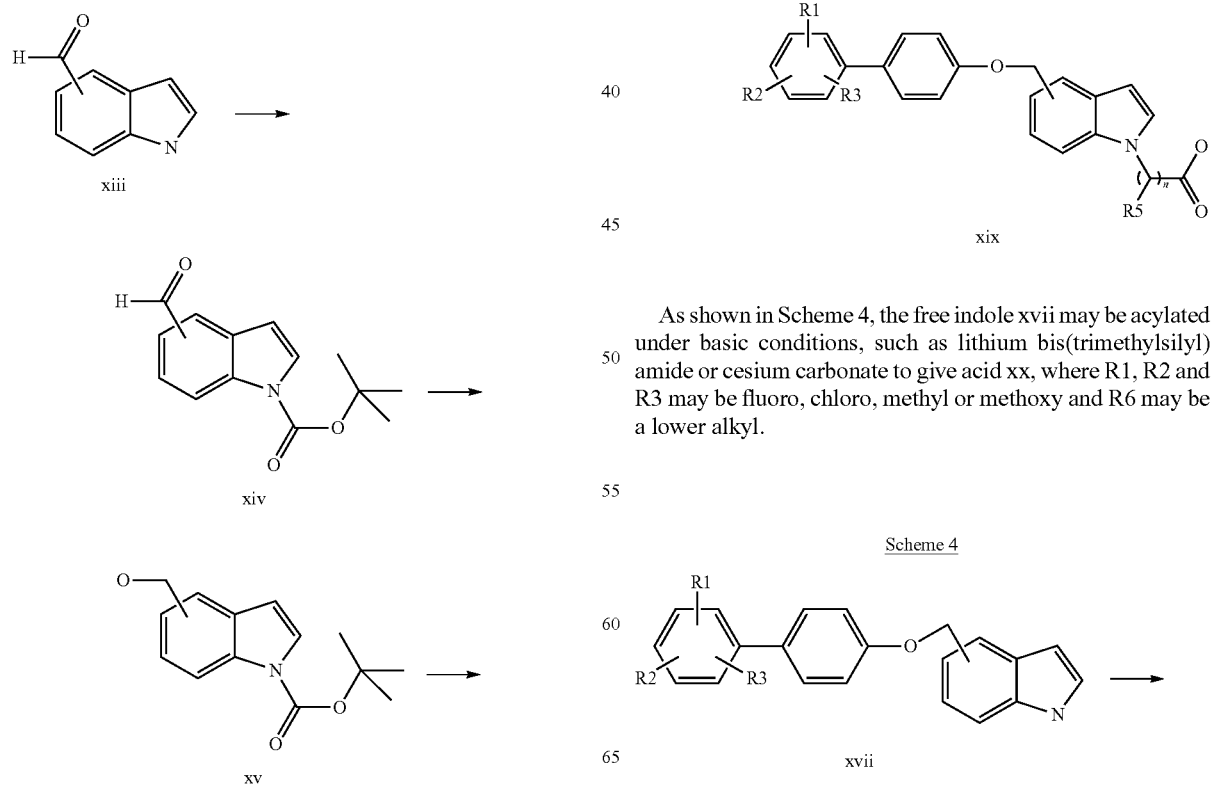

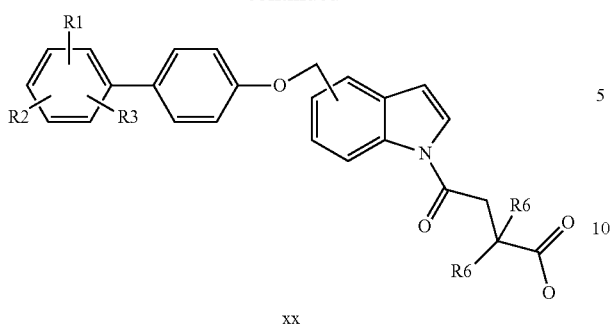

xx

The preparation of substituted 3-amino-indazoles is shown in Scheme 5. 5-Bromomethyl-2-fluoro-benzonitrile xx can be alkylated with a substituted bi-aryl-phenol under basic conditions to form a substituted-bi-phenyloxymethyl-benzonitrile (xxi), which upon heating with hydrazine hydrate or an alkylated hydrazine, can give amino-indazole (xxii), where R1, R2 and R3 may be fluoro, chloro, methyl or methoxy and R7 may be a lower alkyl.

Scheme 5

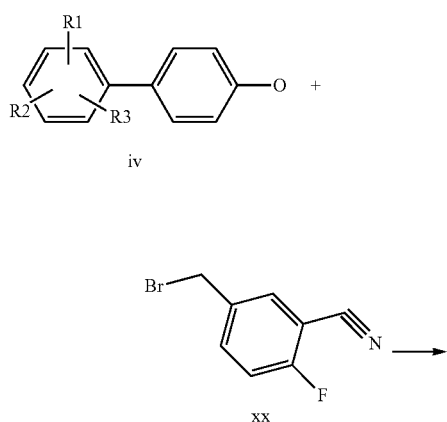

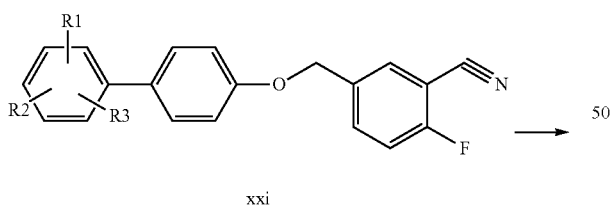

The invention will now be further described in the Examples below, which are intended as an illustration only and do not limit the scope of the invention.

EXAMPLES

Part I

Preparation of Preferred Intermediates

4',5'-Difluoro-2'-methoxy-biphenyl-4-ol

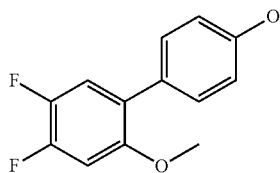

4,5-Difluoro-2-methoxyphenyl-boronic acid (8.8 g, 46.82 mmol) and 4-iodophenol (6.86 g, 31.21 mmol) were suspended in 165 ml of DMF. H$_2$O (40 mL) was added and the mixture was degassed with argon. Finely ground potassium carbonate (13 g, 93.63 mmol) and tetrakis(triphenylphosphine) palladium(0) (1.5 g, 1.29 mmol) were added. The reaction was stirred at 80-85° C. for 1 hr under argon and cooled. The mixture was diluted with ethyl acetate and water. The organic layer was washed with brine, dried and solvents were evaporated. The crude product was purified by flash chromatography, eluting with 0-8% ethyl acetate in hexanes to yield 4',5'-difluoro-2'-methoxy-biphenyl-4-ol (6.58 g, 89.3%). LR-MS (ES) calculated for C13H10F2O2, 236.22; found m/z 235 (M–H).

2',4',5'-Trifluoro-biphenyl-4-ol

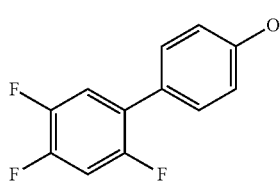

A mixture of 2,4,6-trifluorophenylboronic acid (43.8 g, 249.2 mmol), 4-iodophenol (50 g, 226.5 mmol), potassium carbonate (78 g, 556.3 mmol), Pd (dppf)Cl$_2$ methylene chloride complex (5.5 g, 6.8 mmol), DMF (150 mL), and water (38 mL) was degassed, flashed with nitrogen, and heated at 50° C. overnight. The mixture was then diluted with EtOAc and water, acidified with conc. HCl under cooling with ice-water bath, stirred with charcoal, and filtered through celite. The organic layer was separated, washed with water and brine, dried over sodium sulfate, filtered, and evaporated to afford a deep red oily product. The crude product in EtOAc was passed through a plug of silica gel to give light brown solid product (38 g, 75%). LC-MS (ES) calculated for C12H7F3O, 224; found m/z 224 [M+H]+.

Part II

Preparation of Preferred Embodiments of the Invention

Example 1

4-(4',5'-Difluoro-2'-methoxy-biphenyl-4-yloxymethyl)-1H-indazole

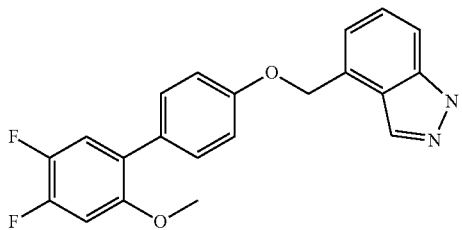

3-Amino-2-methyl benzyl alcohol (0.82 g, 5.98 mmol), acetic anhydride (1.68 mL, 17.8 mmol), potassium acetate (1.75 g, 17.8 mol), isoamyl nitrite (1.82 mL, 13.7 mmol) and 18-crown-6 (79 mg, 0.3 mmol) in 25 mL CHCl3 were reacted as described in EP99/07620. The crude product was purified by flash chromatography with a gradient from 0-35% ethyl acetate in hexanes to yield acetic acid 1-acetyl-1H-indazol-4-ylmethyl ester.

Acetic acid 1-acetyl-1H-indazol-4-ylmethyl ester was treated with 6 mL 48% HBr with stirring overnight and then refluxed for 5 hrs. The reaction mixture was concentrated, diluted with CH3CN and the precipitated solid was filtered off. The residue was treated with dihydropyran (0.53 g, 6.28 mmol) in 25 mL THF and heated to reflux for 5 hrs. The reaction was cooled and distributed between CH2Cl2 and saturated NaHCO3. The organic layer was separated, washed with H2O and concentrated in vacuo. The crude product (2.0 g) was used without further purification.

4-Bromomethyl-1-(tetrahydro-pyran-2-yl)-1H-indazole (0.5 g, 1.69 mmol), 3-(4',5'-difluoro-2'-methoxy-biphenyl-4-ol (0.4 g, 1.69 mmol) and potassium carbonate (0.23 g, 1.69 mmol) in 15 mL THF/3 mL DMF was heated to 70° C. overnight. The reaction was cooled and distributed between EtOAc and H2O. The organic layer was separated and concentrated in vacuo. The crude product was purified by flash chromatography with a gradient from 0-25% ethyl acetate in hexanes to yield 4-(4',5'-difluoro-2'-methoxy-biphenyl-4-yloxymethyl)-1-(tetrahydro-pyran-2-yl)-1H-indazole as a white solid (400 mg, 52.5%). HR-MS (ES) calculated for C26H24F2N2O3, 473.1646; found m/z 473.1647 [M+Na]+.

4-(4',5'-Difluoro-2'-methoxy-biphenyl-4-yloxymethyl)-1-(tetrahydro-pyran-2-yl)-1H-indazole (0.4 g, 0.888 mmol) and 1N HCl (1.8 mL, 1.8 mmol) in 10 mL MeOH were heated to reflux for 5 hrs. The reaction was cooled and distributed between EtOAc and H2O. The water layer was made basic to pH 12 and the organic layer was separated and concentrated in vacuo. The crude product was purified by flash chromatography with a gradient from 20-100% ethyl acetate in hexanes to yield 4-(4',5'-difluoro-2'-methoxy-biphenyl-4-yloxymethyl)-1H-indazole as a white solid (240 mg, 73.7%). LC-MS (ES) calculated for C21H16F2N2O2, 366.37; found m/z 367 [M+H]+.

Example 2

3-[4-(4',5'-Difluoro-2'-methoxy-biphenyl-4-yloxymethyl)-indazol-1-yl]-propionic acid

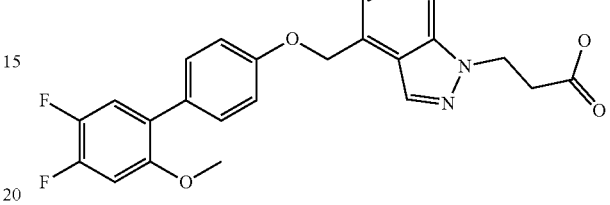

4-(4',5'-Difluoro-2'-methoxy-biphenyl-4-yloxymethyl)-1H-indazole (0.09 g, 0.245 mmol), ethyl bromopropionate (0.045 g, 0.245 mmol), cesium carbonate (81 mg, 0.294 mmol) in 6 mL DMF was stirred at RT overnight and then heated to 90° C. for 35 min. The reaction was cooled and distributed between EtOAc and H2O. The organic layer was separated and concentrated in vacuo. The crude product was purified by flash chromatography with a gradient from 0-30% ethyl acetate in hexanes to yield 3-[4-(4',5'-difluoro-2'-methoxy-biphenyl-4-yloxymethyl)-indazol-1-yl]-propionic acid ethyl ester as a white solid (98 mg, 85.7%).

3-[4-(4',5'-Difluoro-2'-methoxy-biphenyl-4-yloxymethyl)-indazol-1-yl]-propionic acid ethyl ester (0.095 g, 0.204 mmol) and lithium hydroxide hydrate (10 mg, 0.245 mmol) in 5 mL THF/1 mL H2O was stirred at RT for 3 hrs. The reaction was distributed between EtOAc and H2O. The water layer was made acidic to pH 3 with 1N HCl and the organic layer was separated and concentrated in vacuo. The crude product was purified by flash chromatography with a gradient from 0-3% methanol in CH2Cl2 to yield 3-[4-(4',5'-difluoro-2'-methoxy-biphenyl-4-yloxymethyl)-indazol-1-yl]-propionic acid as a white solid (53 mg, 59%). LC-MS (ES) calculated for C24H20F2N2O4, 438.43; found m/z 439 [M+H]+.

Example 3

6-(4',5'-Difluoro-2'-methoxy-biphenyl-4-yloxymethyl)-1H-indazole

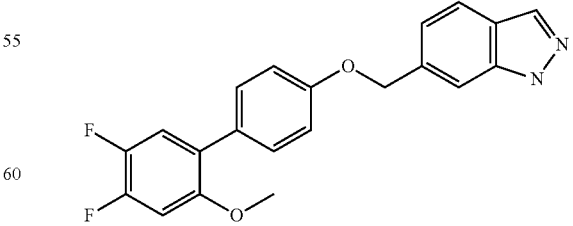

6-(4',5'-Difluoro-2'-methoxy-biphenyl-4-yloxymethyl)-1H-indazole was prepared from 3-amino-4 methyl benzyl alcohol (1 g, 0.729 mmol), as described above for 4-(4',5'-difluoro-2'-methoxy-biphenyl-4-yloxymethyl)-1H-indazole, to yield 510 mg of product. LC-MS (ES) calculated for C21H16F2N2O2, 366.37; found m/z 367 [M+H]+.

Example 4

[6-(4',5'-Difluoro-2'-methoxy-biphenyl-4-yloxymethyl)-indazol-1-yl]-acetic acid

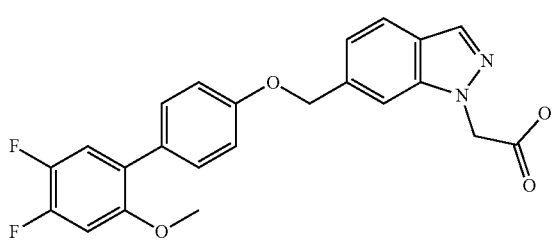

6-(4',5'-Difluoro-2'-methoxy-biphenyl-4-yloxymethyl)-1H-indazole (0.15 g, 0.331 mmol), ethyl bromoacetate (0.055 g, 0.331 mmol), cesium carbonate (119 mg, 0.364 mmol) in 6 mL DMF was stirred at RT overnight and then heated to 90° C. for 35 min. The reaction was cooled and distributed between EtOAc and H2O. The organic layer was separated and concentrated in vacuo. The crude product was purified by flash chromatography with a gradient from 0-30% ethyl acetate in hexanes to yield [6-(4',5'-difluoro-2'-methoxy-biphenyl-4-yloxymethyl)-indazol-1-yl]-acetic acid ethyl ester as a white solid (120 mg, 80.1%).

[6-(4',5'-Difluoro-2'-methoxy-biphenyl-4-yloxymethyl)-indazol-1-yl]-acetic acid ethyl ester (0.095 g, 0.204 mmol) and lithium hydroxide hydrate (10 mg, 0.245 mmol) in 5 mL THF/1 mL H2O was stirred at RT for 6 hrs. The reaction was distributed between EtOAc and H2O. The water layer was made acidic to pH 3 with 1N HCl and the organic layer was separated and concentrated in vacuo. The crude product was purified by trituration with Et2O to yield [6-(4',5'-difluoro-2'-methoxy-biphenyl-4-yloxymethyl)-indazol-1-yl]-acetic acid as a white solid. LC-MS (ES) calculated for C23H18F2N2O4, 424.41; found m/z 425 [M+H]+.

Example 5

3-[6-(4',5'-Difluoro-2'-methoxy-biphenyl-4-yloxymethyl)-indazol-1-yl]-propionic acid

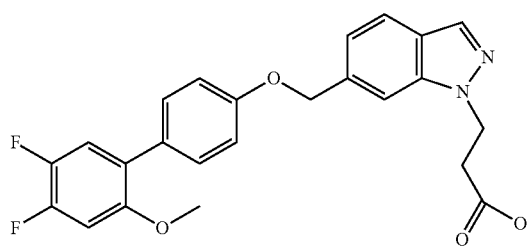

3-[6-(4',5'-Difluoro-2'-methoxy-biphenyl-4-yloxymethyl)-indazol-1-yl]-propionic acid was prepared from 6-(4',5'-difluoro-2'-methoxy-biphenyl-4-yloxymethyl)-1H-indazole (0.1 g, 0.221 mmol) and ethyl bromopropionate (40 mg, 0.221 mmol), as described above for [6-(4',5'-difluoro-2'-methoxy-biphenyl-4-yloxymethyl)-indazol-1-yl]-acetic acid, to yield 81 mg (83.6%) of product. LC-MS (ES) calculated for C24H20F2N2O4, 438.43; found m/z 439 [M+H]+.

Example 6

6-(4',5'-difluoro-2'-methoxy-biphenyl-4-yloxymethyl)-1H-indole

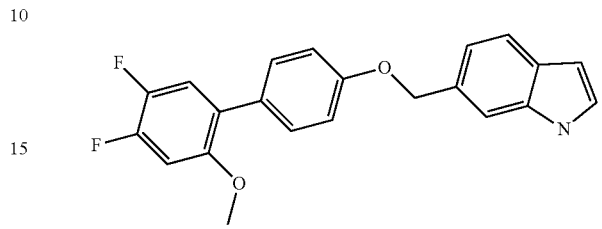

To 1H-Indole-6-carbaldehyde (1 g, 1.3 mmol, 1 eq) in acetonitrile (10 mL) was added potassium carbonate (1.5 g 11 mmol, 1.5 eq) and then di-tert-butyl-dicarbonate (2.39 g, 11 mmol, 1.5 eq). The reaction was heated, tetrahydrofuran (10 mL) was added, and the reaction refluxed for 5 hr. The reaction cooled to RT, diluted with ethyl acetate (150 mL) washed with NaCl solution (100 mL water, 100 mL brine), dried over sodium sulfate, concentrated, adsorbed onto silica gel and purified by flash chromatography with a gradient from 1-10% ethyl acetate in hexanes to yield 6-formyl-indole-1-carboxylic acid tert-butyl ester as a yellow, viscous oil (1.2 g). LC-MS (ES) calculated for C14H15NO3, 245.1; found m/z 246 [M+H]+.

To 6-formyl-indole-1-carboxylic acid tert-butyl ester (1.2 g) in methanol (5 mL) in an ice bath was added sodium borohydride (0.27 mg) portion wise. The reaction was allowed to warm to room temperature over 1.5 hr. The reaction diluted with ethyl acetate (200 mL) washed with water (200 mL), brine (100 mL), dried over sodium sulfate, concentrated, adsorbed onto silica gel and purified by flash chromatography with a gradient from 5-40% ethyl acetate in hexanes to yield 6-hydroxymethyl-indole-1-carboxylic acid tert-butyl ester as a clear viscous oil (0.91 g, 78%) LC-MS (ES) calculated for C14H17NO3, 247.1; found m/z 246 [M−H]−.

To 4',5'-difluoro-2'-methoxy-biphenyl-4-ol (472 mg, 2 mmol, 2 eq) was added polymer-bound triphenyl-phosphine (667 mg, 2 mmol, 2 eq) and dichloromethane (10 mL). The mixture was placed under nitrogen, cooled in an ice bath, diisopropyl azodicarboxylate (0.394 mL, 2 mmol, 2 eq) was added drop-wise, stirred for 1.5 hr. A solution of 6-hydroxymethyl-indole-1-carboxylic acid tert-butyl ester (247 mg, 1 mmol, 1 eq) and triethylamine (0.279 mL, 2 mmol, 2 eq) in dichloromethane (2 mL) was added drop to portion wise and the reaction allowed to warm to room temperature overnight (20 hr). The reaction was filtered over Celite, adsorbed onto silica gel, and purified by flash chromatography with a gradient from 1-15% ethyl acetate in hexanes to yield 6-(4',5'-difluoro-2'-methoxy-biphenyl-4-yloxymethyl)-indole-1-carboxylic acid tert-butyl ester white/clear solid (288 mg, 62%). LC-MS (ES) calculated for C27H25F2NO2, 465.2; found m/z 466 [M+H]+.

To 6-(4',5'-difluoro-2'-methoxy-biphenyl-4-yloxymethyl)-indole-1-carboxylic acid tert-butyl ester (232 mg, 0.5 mmol) was added methanol and the mixture was microwaved at 150° C. for 30 min. The reaction was concentrated and dried from dichloromethane to yield 6-(4',5'-difluoro-2'-methoxy-biphenyl-4-yloxymethyl)-1H-indole as a white

Example 7

3-[6-(4',5'-Difluoro-2'-methoxy-biphenyl-4-yloxymethyl)-indol-1-yl]-propionic Acid

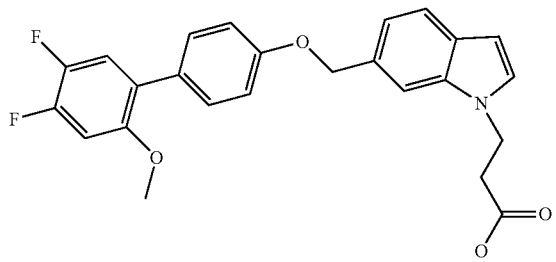

To 6-(4',5'-difluoro-2'-methoxy-biphenyl-4-yloxymethyl)-1H-indole (37 mg, 0.10 mmol, 1 eq.) was added dimethylformamide (1 mL), cesium carbonate (40 mg, 0.11 mmol, 1.1 eq.) and 3-bromo-propionic acid ethyl ester (0.014 mL, 0.11 mmol, 1.1 eq.). The reaction was stirred and heated at 90° C. for 17 hr. The reaction was diluted with dimethylsulfoxide, filtered, and purified by HPLC with a 50-100% acetonitrile in water gradient to yield 3-[6-(4',5'-difluoro-2'-methoxy-biphenyl-4-yloxymethyl)-indol-1-yl]-propionic acid ethyl ester as clear oil (33 mg, 73%). LC-MS (ES) calculated for C27H25F2NO4, 465.2; found m/z 466 [M+H]$^+$.

To 3-[6-(4',5'-difluoro-2'-methoxy-biphenyl-4-yloxymethyl)-indol-1-yl]-propionic acid ethyl ester (24 mg, 0.051 mmol, 1 eq.) was added tetrahydrofuran (1 mL), water (1 mL) and lithium hydroxide (LiOH—H$_2$O (4.5 mg, 0.1 mmol, 2.2 eq.). The reaction was stirred and at room temperature for 2 and then DOWEX resin (50WX4-400, acid washed, 2 g) was added. The mixture was stirred at room temperature, filtered, dried, and then lyophilized from acetonitrile/water to yield 3-[6-(4',5'-difluoro-2'-methoxy-biphenyl-4-yloxymethyl)-indol-1-yl]-propionic acid as an off-white solid (23 mg, 98%). LC-MS (ES) calculated for C25H21F2NO4, 437.12; found m/z 438 [M+H]$^+$.

Example 8

[6-(4',5'-Difluoro-2'-methoxy-biphenyl-4-yloxymethyl)-indol-1-yl]-Acetic Acid

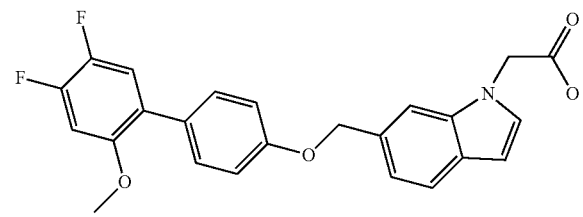

[6-(4',5'-Difluoro-2'-methoxy-biphenyl-4-yloxymethyl)-indol-1-yl]-acetic acid ethyl ester was synthesized by a procedure similar to 3-[6-(4',5'-difluoro-2'-methoxy-biphenyl-4-yloxymethyl)-indol-1-yl]-propionic acid ethyl ester from starting materials 6-(4',5'-difluoro-2'-methoxy-biphenyl-4-yloxymethyl)-1H-indole and bromo-acetic acid ethyl ester to yield the product as a white solid/wax (25 mg, 56%). LC-MS (ES) calculated for C26H23F2NO4, 451.2; found m/z 452 [M+H]$^+$.

[6-(4',5'-Difluoro-2'-methoxy-biphenyl-4-yloxymethyl)-indol-1-yl]-acetic acid was synthesized by a procedure similar to 3-[6-(4',5'-difluoro-2'-methoxy-biphenyl-4-yloxymethyl)-indol-1-yl]-propionic acid from starting material [6-(4',5'-difluoro-2'-methoxy-biphenyl-4-yloxymethyl)-indol-1-yl]-acetic acid ethyl ester to yield the product as a white solid (23 mg, 82%). LC-MS (ES) calculated for C24H19F2NO4, 423.1; found m/z 424 [M+H]$^+$.

Example 9

3-[6-(4',5'-Difluoro-2'-methoxy-biphenyl-4-yloxymethyl)-indol-1-yl]-butyric Acid

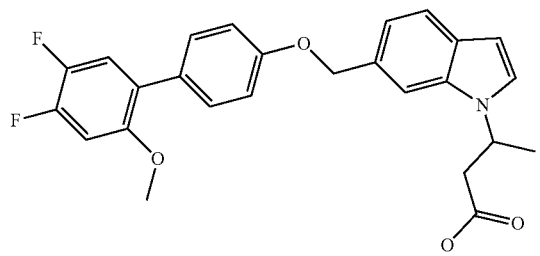

To 6-(4',5'-difluoro-2'-methoxy-biphenyl-4-yloxymethyl)-1H-indole (37 mg, 0.10 mmol, 1 eq.) was added dimethylformamide (1 ml), sodium hydride (8 mg of 60% dispersion, 0.2 mmol, 2 eq.) and (E)-but-2-enoic acid ethyl ester (0.025 ml, 0.2 mmol, 2 eq.). The reaction was stirred at room temperature for 18 hr and heated at 50° C. for 2 hr. To the reaction was added more (E)-but-2-enoic acid ethyl ester (0.050 ml, 0.4 mmol, 4 eq.) and the reaction heated at 80° C. for 22 hr. The reaction was partitioned between ethyl acetate (10 mL) and aqueous citric acid (10 mL), the organic layer separated and washed with brine (saturated NaCl), dried over magnesium sulfate, filtered, evaporated under reduced pressure. The crude material was dissolved in dimethylsulfoxide and purified by HPLC with a 50-100% acetonitrile in water gradient to yield 3-[6-(4',5'-difluoro-2'-methoxy-biphenyl-4-yloxymethyl)-indol-1-yl]-butyric acid as white solid (3 mg, 6%). LC-MS (ES) calculated for C26H23F2NO4, 451.2; found m/z 452 [M+H]$^+$.

Example 10

4-(4',5'-Difluoro-2'-methoxy-biphenyl-4-yloxymethyl)-1H-indole

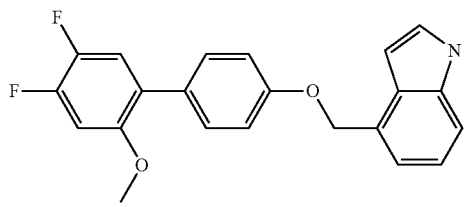

4-Formyl-indole-1-carboxylic acid tert-butyl ester was synthesized by a procedure similar to 6-Formyl-indole-1-carboxylic acid tert-butyl ester from starting materials 1H-Indole-4-carbaldehyde and di-tert-butyl-dicarbonate to yield the product as a clear yellow oil (2 g, 80%). LC-MS (ES) calculated for C14H15NO3, 245.1; found m/z 244 [M−H]⁻.

4-Hydroxymethyl-indole-1-carboxylic acid tert-butyl ester was synthesized by a procedure similar to 6-hydroxymethyl-indole-1-carboxylic acid tert-butyl ester from starting material 4-formyl-indole-1-carboxylic acid tert-butyl ester to yield the product as a clear viscous oil (0.91 g, 78%). LC-MS (ES) calculated for C14H17NO3, 247.1; found m/z 246 [M+H]⁺.

4-(4',5'-difluoro-2'-methoxy-biphenyl-4-yloxymethyl)-indole-1-carboxylic acid tert-butyl ester was synthesized by a procedure similar to 6-(4',5'-difluoro-2'-methoxy-biphenyl-4-yloxymethyl)-indole-1-carboxylic acid tert-butyl ester from starting materials 4-hydroxymethyl-indole-1-carboxylic acid tert-butyl ester and 4',5'-difluoro-2'-methoxy-biphenyl-4-ol to yield the product as a white solid (880 mg, 70%). LC-MS (ES) calculated for C27H25F2NO2, 465.2; found m/z 466 [M+H]⁺.

4-(4',5'-Difluoro-2'-methoxy-biphenyl-4-yloxymethyl)-1H-indole was synthesized by a procedure similar to 6-(4',5'-difluoro-2'-methoxy-biphenyl-4-yloxymethyl)-1H-indole from starting material 4-(4',5'-difluoro-2'-methoxy-biphenyl-4-yloxymethyl)-indole-1-carboxylic acid tert-butyl ester to yield the product was a white solid (156 mg, 99%). LC-MS (ES) calculated for C22H17F2NO2, 365.1; found m/z 366 [M+H]⁺.

Example 11

4-[4-(4',5'-Difluoro-2'-methoxy-biphenyl-4-yloxymethyl)-indol-1-yl]-4-oxo-butyric acid

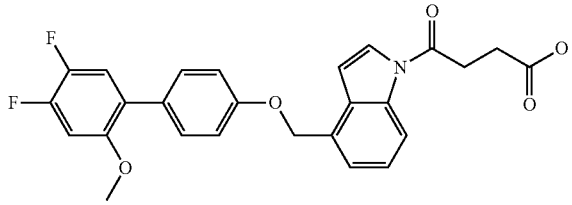

To 4-(4',5'-difluoro-2'-methoxy-biphenyl-4-yloxymethyl)-1H-indole (37 mg, 0.10 mmol, 1 eq.) was added dimethylformamide (1 mL), triethylamine (0.154 ml, 1.1 mmol, 10 eq.) and succinic anhydride (30 mg, 0.3 mmol, 3 eq.) the reaction was stir at 80° C. for 8 hr and allowed to cool to room temperature. Lithium bis(trimethylsilyl)amide (1 M in THF, 1.2 mL, 1.2 mmol, 12 eq) was added and the reaction was allowed to proceed at room temperature for 24 hr. The reaction was purified by HPLC with a 30-100% acetonitrile in water gradient and dried from dichloromethane/hexanes mixture to yield 4-[4-(4',5'-difluoro-2'-methoxy-biphenyl-4-yloxymethyl)-indol-1-yl]-4-oxo-butyric acid as a white solid (16 mg, 34%). LC-MS (ES) calculated for C26H21F2NO5, 465.1; found m/z 466 [M+H]⁺.

Example 12

4-[4-(4',5'-Difluoro-2'-methoxy-biphenyl-4-yloxymethyl)-indol-1-yl]-2,2-dimethyl-4-oxo-butyric acid

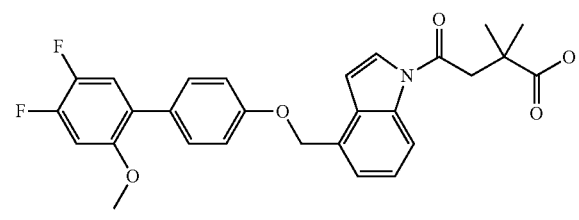

4-[4-(4',5'-Difluoro-2'-methoxy-biphenyl-4-yloxymethyl)-indol-1-yl]-2,2-dimethyl-4-oxo-butyric acid was synthesized by a procedure similar to 4-[4-(4',5'-difluoro-2'-methoxy-biphenyl-4-yloxymethyl)-indol-1-yl]-4-oxo-butyric acid from starting materials 4-(4',5'-difluoro-2'-methoxy-biphenyl-4-yloxymethyl)-1H-indole and 2,2-dimethyl-succinic anhydride to yield the product as a white solid (13 mg, 27%). LC-MS (ES) calculated for C28H25F2NO5, 493.2; found m/z 494 [M+H]⁺.

Example 13

[4-(4',5'-Difluoro-2'-methoxy-biphenyl-4-yloxymethyl)-indol-1-yl]-acetic acid

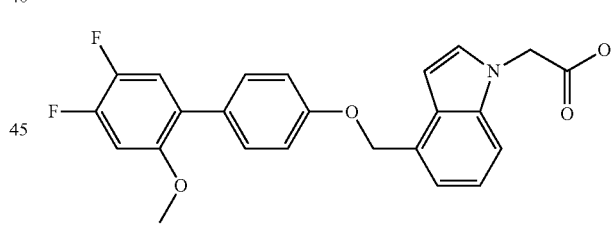

[4-(4',5'-Difluoro-2'-methoxy-biphenyl-4-yloxymethyl)-indol-1-yl]-acetic acid ethyl ester was synthesized by a procedure similar to 3-[6-(4',5'-difluoro-2'-methoxy-biphenyl-4-yloxymethyl)-indol-1-yl]-propionic acid ethyl ester from starting materials 4-(4',5'-difluoro-2'-methoxy-biphenyl-4-yloxymethyl)-1H-indole and bromo-acetic acid ethyl ester to yield the product as a white solid/wax (30 mg, 66%). LC-MS (ES) calculated for C26H23F2NO4, 451.2; found m/z 452 [M+H]⁺.

[4-(4',5'-Difluoro-2'-methoxy-biphenyl-4-yloxymethyl)-indol-1-yl]-acetic acid was synthesized by a procedure similar to 3-[6-(4',5'-difluoro-2'-methoxy-biphenyl-4-yloxymethyl)-indol-1-yl]-propionic acid from starting material [4-(4',5'-difluoro-2'-methoxy-biphenyl-4-yloxymethyl)-indol-1-yl]-acetic acid ethyl ester to yield the product as a white solid (23 mg, 82%). LC-MS (ES) calculated for C24H19F2NO4, 423.1; found m/z 424 [M+H]+.

Example 14

3-[4-(4',5'-Difluoro-2'-methoxy-biphenyl-4-yloxymethyl)-indol-1-yl]-propionic acid

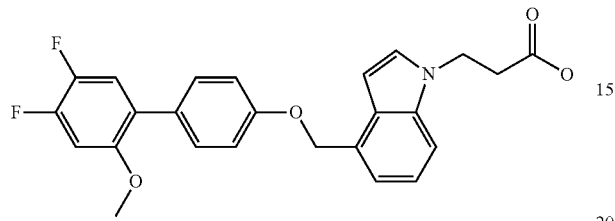

3-[4-(4',5'-Difluoro-2'-methoxy-biphenyl-4-yloxymethyl)-indol-1-yl]-propionic acid ethyl ester was synthesized by a procedure similar to 3-[6-(4',5'-difluoro-2'-methoxy-biphenyl-4-yloxymethyl)-indol-1-yl]-propionic acid ethyl ester from starting materials 4-(4',5'-difluoro-2'-methoxy-biphenyl-4-yloxymethyl)-1H-indole and 3-bromo-propionic acid ethyl ester to yield the product as a clear to opaque oil/film (30 mg, 65%). LC-MS (ES) calculated for C27H25F2NO4, 465.2; found m/z 466 [M+H]+.

3-[4-(4',5'-Difluoro-2'-methoxy-biphenyl-4-yloxymethyl)-indol-1-yl]-propionic acid was synthesized by a procedure similar to 3-[6-(4',5'-difluoro-2'-methoxy-biphenyl-4-yloxymethyl)-indol-1-yl]-propionic acid from starting material 3-[4-(4',5'-difluoro-2'-methoxy-biphenyl-4-yloxymethyl)-indol-1-yl]-propionic acid ethyl ester to yield the product as a white solid (23 mg, 82%). LC-MS (ES) calculated for C25H21F2NO4, 437.1; found m/z 438 [M+H]+.

Example 15

3-[4-(4',5'-Difluoro-2'-methoxy-biphenyl-4-yloxymethyl)-indol-1-yl]-butyric acid

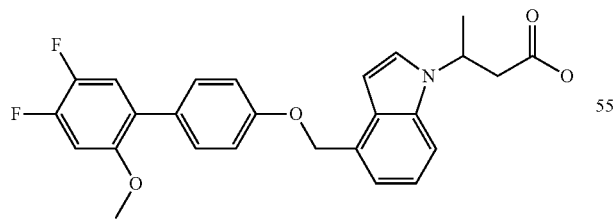

3-[4-(4',5'-Difluoro-2'-methoxy-biphenyl-4-yloxymethyl)-indol-1-yl]-butyric acid was synthesized by a procedure similar to 3-[6-(4',5'-difluoro-2'-methoxy-biphenyl-4-yloxymethyl)-indol-1-yl]-butyric acid from starting materials 4-(4',5'-difluoro-2'-methoxy-biphenyl-4-yloxymethyl)-1H-indole and (E)-but-2-enoic acid ethyl ester to yield the product as a clear to opaque oil/film (6 mg, 13%). LC-MS (ES) calculated for C26H23F2NO4, 451.2; found m/z 452 [M+H]+.

Example 16

5-(4',5'-Difluoro-2'-methoxy-biphenyl-4-yloxymethyl)-1H-indazol-3-ylamine

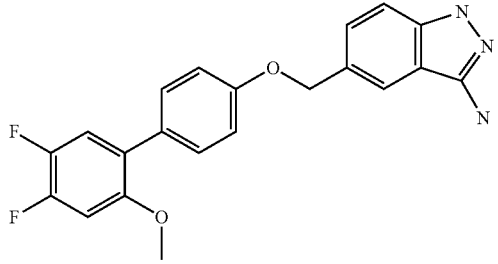

A mixture of 4',5'-difluoro-2'-methoxy-biphenyl-4-ol (2 g, 8.5 mmol), 5-bromomethyl-2-fluoro-benzonitrile (2 g, 9.3 mmol), potassium carbonate (3.5 g, 25.4 mmol) and DMF (50 mL) was stirred at room temperature overnight. The mixture was then diluted with EtOAc, followed by washing with water and brine, dried over sodium sulfate, filtered, and evaporated. The residue was purified by flash column chromatography (0-20% EtOAc in hexane) to give title compound. LC-MS (ES) calculated for C21H14F3NO2, 369.35; found m/z 370 [M+H]+.

A mixture of 2-fluoro-5-(4',5'-difluoro-2'-methoxy-biphenyl-4-yloxymethyl)-benzonitrile (150 mg, 0.41 mmol), aqueous hydrazine (excess) and n-butanol (3 mL) was heated to 150° C. for 30 min via microwave reactor. The mixture was then cooled to room temperature. The mixture was then purified by preparative HPLC under neutral conditions to give title compound. LC-MS (ES) calculated for C21H17F2N3O2, 381.39; found m/z 382 [M+H]+.

Example 17

Methyl-5-(2',4',5'-trifluoro-biphenyl-4-yloxymethyl)-1H-indazol-3-ylamine

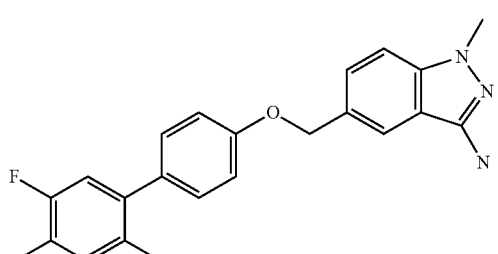

A mixture of 2',4',5'-trifluoro-biphenyl-4-ol (8.4 g, 37.4 mmol), 5-bromomethyl-2-fluoro-benzonitrile (4 g, 18.7 mmol), potassium carbonate (10.3 g, 74.8 mmol) and DMF (50 mL) was stirred at room temperature over the weekend. The mixture was then diluted with EtOAc, followed by washing with water and brine, dried over sodium sulfate, filtered, and evaporated. The residue was purified by flash column chromatography (0-15% EtOAc in hexane) to give title compound. LC-MS (ES) calculated for C20H11F4NO, 357.31; found m/z 358 [M+H]+.

A mixture of 2-fluoro-5-(2',4',5'-trifluoro-biphenyl-4-yloxymethyl)-benzonitrile (500 mg, 1.4 mmol), methylhydrazine (644 mg, 14 mmol) and n-butanol (10 mL) was heated to 150° C. for 1 h via microwave reactor. The mixture was then cooled to room temperature. The white solid was collected by filtration, washed with cold MeOH to afford title compound. LC-MS (ES) calculated for C21H16F3N3O, 383.38; found m/z 384 [M+H]+.

Example 18

Glycogen Synthase (GS) Assay

The following tests were carried out in order to determine the activity of the compounds of formula (I).

Twelve μL per well of substrate solution containing glycogen (4.32 mg/ml), 2.67 mM UDP-glucose, 21.6 mM phospho(enol)pyruvate and 2.7 mM NADH in 30 mM glycylglycine, pH 7.3 buffer was added into a polystyrene 384-well assay plate (BD Biosciences).

Compound solutions (8 μL/well) at various concentrations (0-300 μM) were added to the assay plate (columns 5-24). Compound solution contains 30 mM glycylglycine, pH 7.3, 40 mM KCl, 20 mM MgCl$_2$, 9.2% DMSO, with (columns 15-24) or without (columns 5-14) 20 mM glucose 6-phosphate.

Enzyme solution (12 μL/well) containing glycogen synthase (16.88 μg/ml), pyruvate kinase (0.27 mg/ml), lactate dehydrogenase (0.27 mg/ml) in 50 mM Tris-HCl, pH 8.0, 27 mM DTT and bovine serum albumin (BSA, 0.2 mg/ml) was added to the assay plate (columns 3-24). As a blank control, enzyme solution without glycogen synthase was added into the top half wells of columns 1-2. To the bottom half wells of columns 1-2 were added a known activator, glucose 6-phosphate (at final concentration 5 mM) in addition to the enzyme solution. The reaction mixture was incubated at room temperature. The assay plate was then read for absorbance at 340 nm on an Envision reader every 3 minutes up to a total of 15 minutes.

The enzyme activity (with or without compound) was calculated by the reaction rate and represented by the optical density change (δOD) per minute. Percent stimulation of glycogen synthase activity by a compound at various concentrations was calculated by the following formula:

% stimulation=100*Rs/Rt, wherein Rs is the reaction rate of the enzyme in the presence of compound and Rt is the reaction rate of the enzyme in the absence of compound.

SC$_{200}$ is defined as the compound concentration that is needed to stimulate 200% of the enzyme activity. EC$_{50}$ is defined as the compound concentration that is needed to give 50% maximum activation.

Compounds from Example 1 through Example 17 were assayed according to assay procedures described above and the results are listed in Table 1 below:

TABLE 1

| Glycogen Synthase Activation Potency | | |
|---|---|---|
| Example Number | GS SC$_{200}$ (μM) | GS EC$_{50}$ (μM) |
| 1 | 4.57 | 6.56 |
| 2 | 5.52 | 26 |

TABLE 1-continued

| Glycogen Synthase Activation Potency | | |
|---|---|---|
| Example Number | GS SC$_{200}$ (μM) | GS EC$_{50}$ (μM) |
| 3 | 3.92 | 6 |
| 4 | 2.56 | 7 |
| 5 | 0.28 | 1.43 |
| 6 | 5.3 | 5.37 |
| 7 | 0.6 | 3 |
| 8 | 2 | 5.16 |
| 9 | 0.41 | 2.01 |
| 10 | 2.86 | 3.88 |
| 11 | 0.44 | 2.46 |
| 12 | 1.19 | 3.04 |
| 13 | 0.43 | 3.12 |
| 14 | 1.46 | 5.49 |
| 15 | 2.29 | 6.67 |
| 16 | 0.6 | 2.79 |
| 17 | 3.9 | 18.5 |

It is to be understood that the invention is not limited to the particular embodiments of the invention described above, as variations of the particular embodiments may be made and still fall within the scope of the appended claims.

What is claimed is:
1. A compound of formula (I):

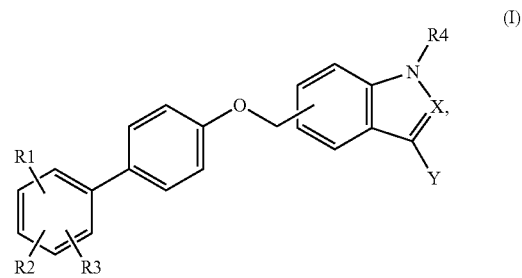

wherein,
R1, R2, R3, independently of each other, is hydrogen, halogen, lower alkyl or alkoxy;
R4 is hydrogen, unsubstituted lower alkyl, or lower alkyl substituted with one to four substituents independently selected from the group consisting of methyl, (=O) and —COOH;
X is CH or N; and
Y is hydrogen or —NH$_2$,
or a pharmaceutically acceptable salt thereof.

2. The compound according to claim 1, wherein R1, R2, R3, independently of each other, is halogen, lower alkyl or alkoxy.

3. The compound according to claim 1, wherein R1, R2, R3, independently of each other, is fluorine, chlorine, methyl or methoxy.

4. The compound according to claim 1, wherein R1 and R2 are halogen.

5. The compound according to claim 1, wherein R1 is fluorine or chlorine.

6. The compound according to claim 1, wherein R2 is fluorine or chlorine.

7. The compound according to claim 1, wherein R3 is halogen or alkoxy.

8. The compound according to claim 1, wherein R3 is fluorine or methoxy.

9. The compound according to claim 1, wherein R4 is lower alkyl substituted with one to four substituents independently selected from the group consisting of methyl, (═O) and —COOH.

10. The compound according to claim 1, wherein R4 is:

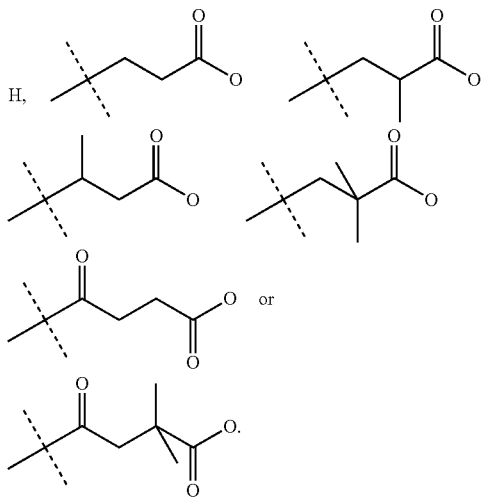

11. The compound according to claim 1, wherein X is CH.
12. The compound according to claim 1, wherein X is N.
13. The compound according to claim 1, wherein Y is hydrogen.
14. The compound according to claim 1, wherein Y is —NH$_2$.
15. The compound according to claim 1, wherein said compound is:

4-(4',5'-Difluoro-2'-methoxy-biphenyl-4-yloxymethyl)-1H-indazole;

3-[4-(4',5'-Difluoro-2'-methoxy-biphenyl-4-yloxymethyl)-indazol-1-yl]-propionic acid;

6-(4',5'-Difluoro-2'-methoxy-biphenyl-4-yloxymethyl)-1H-indazole;

[6-(4',5'-Difluoro-2'-methoxy-biphenyl-4-yloxymethyl)-indazol-1-yl]-acetic acid;

3-[6-(4',5'-Difluoro-2'-methoxy-biphenyl-4-yloxymethyl)-indazol-1-yl]-propionic acid;

6-(4',5'-difluoro-2'-methoxy-biphenyl-4-yloxymethyl)-1H-indole;

3-[6-(4',5'-Difluoro-2'-methoxy-biphenyl-4-yloxymethyl)-indol-1-yl]-propionic acid;

[6-(4',5'-Difluoro-2'-methoxy-biphenyl-4-yloxymethyl)-indol-1-yl]-acetic acid;

3-[6-(4',5'-Difluoro-2'-methoxy-biphenyl-4-yloxymethyl)-indol-1-yl]-butyric acid;

4-(4',5'-Difluoro-2'-methoxy-biphenyl-4-yloxymethyl)-1H-indole;

4-[4-(4',5'-Difluoro-2'-methoxy-biphenyl-4-yloxymethyl)-indol-1-yl]-4-oxo-butyric acid;

4-[4-(4',5'-Difluoro-2'-methoxy-biphenyl-4-yloxymethyl)-indol-1-yl]-2,2-dimethyl-4-oxo-butyric acid;

[4-(4',5'-Difluoro-2'-methoxy-biphenyl-4-yloxymethyl)-indol-1-yl]-acetic acid;

3-[4-(4',5'-Difluoro-2'-methoxy-biphenyl-4-yloxymethyl)-indol-1-yl]-propionic acid;

3-[4-(4',5'-Difluoro-2'-methoxy-biphenyl-4-yloxymethyl)-indol-1-yl]-butyric acid;

5-(4',5'-Difluoro-2'-methoxy-biphenyl-4-yloxymethyl)-1H-indazol-3-ylamine; or

Methyl-5-(2',4',5'-trifluoro-biphenyl-4-yloxymethyl)-1H-indazol-3-ylamine.

16. A pharmaceutical composition, comprising a therapeutically effective amount of a compound according to claim 1, or a pharmaceutically acceptable salt thereof, and a pharmaceutically acceptable carrier and/or adjuvant.

* * * * *